United States Patent [19]

Fountain et al.

[11] Patent Number: 5,354,353
[45] Date of Patent: Oct. 11, 1994

[54] AMALGAMABLE COMPOSITION AND METHOD OF PRODUCTION

[75] Inventors: Richard W. Fountain, Pinckney; Kamal Asgar, Ann Arbor, both of Mich.

[73] Assignee: Special Metals Corporation, New Hartford, N.Y.

[21] Appl. No.: 142,021

[22] Filed: Oct. 28, 1993

[51] Int. Cl.$^5$ .............................................. B22F 9/02
[52] U.S. Cl. ...................... 75/338; 75/351; 75/388
[58] Field of Search ............... 75/338, 339, 351, 352, 75/355, 388

[56] References Cited

U.S. PATENT DOCUMENTS

| | | | |
|---|---|---|---|
| 3,723,092 | 3/1973 | Benjamin | 75/352 |
| 3,871,876 | 3/1975 | Asgar et al. | 420/527 |
| 3,997,327 | 12/1976 | Tolliver et al. | 75/255 |
| 3,997,329 | 12/1976 | Aliotta et al. | 75/255 |
| 3,997,330 | 12/1976 | Aliotta et al. | 75/255 |
| 4,234,339 | 11/1980 | Aliotta et al. | 75/255 |
| 4,235,631 | 11/1980 | Aliotta et al. | 75/255 |
| 4,374,085 | 2/1983 | Asgar et al. | 420/470 |
| 4,479,823 | 10/1984 | Hohmann | 75/338 |
| 4,664,629 | 5/1987 | Chodkowski | 75/255 |
| 4,664,855 | 5/1987 | Tremblay et al. | 264/11 |
| 4,668,282 | 5/1987 | Gilman et al. | 75/352 |

FOREIGN PATENT DOCUMENTS 58-56741 12/1983 Japan.

OTHER PUBLICATIONS

"Measurement of Resistance of Amalgam Mixes to Condensation," H. Ogura, F. Hadavi, and K. Asgar, Journal of Dental Research, Aug., 1983.

"Marginal Leakage of Dental Amalgam," F. Fanian, F. Hadavi, and K. Asgar, Aug. 11, 1983 Issue of Operative Dentistry.

*Primary Examiner*—George Wyszomierski
*Attorney, Agent, or Firm*—Robert F. Dropkin

[57] ABSTRACT

A multi-component composition suitable for amalgamation with mercury to form a dental amalgam, an amalgam and a method for producing such a multi-component composition. The multi-component composition has: from 30 to 90% (by weight) of a first component containing at least 30% silver, at least 20% tin and at least 10% copper; from 10 to 70% (by weight) of a second component containing at least 30% silver, at least 20% tin and at least 10% copper; and up to 15% (by weight) of a third component containing silver and/or alloy powder containing at least 80% (by weight) silver. The first component is spherically shaped atomized alloy powder. The second component is mechanically worked atomized alloy powder. The surface area to volume ratio of the powder of the second component is greater than the surface area to volume ratio of the powder of the first component.

6 Claims, No Drawings

AMALGAMABLE COMPOSITION AND METHOD OF PRODUCTION

The present invention relates to a multi-component composition, and in particular, to a multi-component composition suitable for amalgamation with mercury to form a dental amalgam, to the amalgam formed therefrom, and to a method for producing such a multi-component composition.

Amalgamable dental alloys are basically alloys of silver and tin with typical additions of copper and possible additions of other elements such as indium, zinc, and palladium. These alloys are supplied to dentists in particle form. Dentists add mercury to the alloy particles and triturate the mixture in an amalgamator to form an amalgamated mass which they, in turn, condense into cavities. Mercury reacts with silver and tin, forming compounds of silver-mercury and tin-mercury. The amount of mercury added by the dentist is not, however, sufficient to complete the reaction. As a result, mercury only reacts with the surface of the alloy particles. The core of the particle remains in the unreacted state. The amalgamated mass placed by a dentist in a cavity is, after hardening, therefore, a heterogeneous material of at least three distinct phases: silver-mercury; tin-mercury; and silver-tin. The phases are, respectively, for convenience purposes called gamma one, gamma two and gamma. When properties of the three phases are compared, it is found that strength and corrosion resistance are highest for the gamma phase and lowest for the gamma two phase. Relative ratios of these three phases, as well as the shape of the original alloy particles that are left in the final product, determine the physical properties of amalgamated dental alloys as well as their ease of manipulation. Alloy particles are typically spherical or irregular in shape.

U.S. Pat. No. 3,871,876 discloses an amalgamable alloy produced through gas atomization and, more particularly, particles of amalgamable alloy which are spherical in shape. The alloy of the patent is, on the one hand, known for smooth, strong and corrosion resistant dental restorations; and, on the other hand, for difficulties encountered in condensing it. Many dentists find that the spherical particles feel too soft and delicate to them insofar as the particles have a tendency to be forced up the sides of a cavity if too much pressure is exerted.

An attempt to improve upon the alloy of U.S. Pat. No. 3,871,876 is disclosed in U.S. Pat. No. 3,997,329. Irregularly shaped particles are mixed with the spherical particles of U.S. Pat. No. 3,871,876 to improve the condensing characteristics of the alloy. The irregular particles are typically lathe-cut.

The addition of the lathe-cut particles of U.S. Pat. No. 3,997,329 to the spherical particles of U.S. Pat. No. 3,871,876 as taught in U.S. Pat. No. 3,997,329 did, in fact, produce an alloy with better condensing characteristics. Unfortunately, certain disadvantages are associated with lathe-cut particles. Lathe-cut particles are characterized by a high percentage of oxides and other undesirable elements and by minute cracks. Their dirty surfaces can slow down a reaction with mercury when mercury is trapped in the cracks. This results in lower initial physical properties.

Other patents disclosing dental alloys formed from mixtures of spherical particles and lathe-cut particles are U.S. Pat. Nos. 3,997,327; 3,997,330; 4,234,339; and 4,664,629. U.S. Pat. No. 4,664,629 discloses a composition which is taught in U.S. Pat. No. 4,374,085.

Through the present invention, there is provided an atomized multi-component composition, and a method for producing such, which upon amalgamation with mercury produces a dental amalgam having compressive strength, creep and condensation resistance comparable or better to that formed from the amalgamation of dental alloys comprised of both spherical and lathe-cut particles, but yet a composition which is free of lathe-cut particles with their inherent disadvantages. There is also provided a multi-component composition which through the addition of a high silver alloy produces restorations characterized by reduced leakage.

An attempt to produce an atomized composition with characteristics comparable to that of the present invention is disclosed in U.S. Pat. Nos. 4,235,631 and 4,664,855. Although U.S. Pat. No. 4,664,855 does disclose the addition of a high silver material to a dental composition, as does Japanese Patent Publication No. 58-56741, neither it nor U.S. Pat. No. 4,235,631 discloses a composition containing spherical particles which significantly contribute to the strength of amalgam restorations. This is clearly evident from U.S. Pat. No. 4,664,855 where the highest disclosed one hour compressive strength is 26,000 pounds per square inch.

It is, moreover, interesting to note that the shortcomings inherent in the use of lathe-cut particles have not been remedied until the advent of the present invention. This is true despite the fact that dental alloys containing both lathe-cut particles and spherical particles have been known for approximately thirty years or more.

It is accordingly an object of the present invention to provide a multi-component composition suitable for amalgamation with mercury to form a dental amalgam.

It is accordingly a further object of the present invention to provide an amalgam formed upon amalgamation of the multi-component composition of the present invention.

It is accordingly a still further object of the present invention to provide a method for producing a multi-component composition suitable for amalgamation with mercury to form a dental amalgam.

The present invention provides a multi-component composition suitable for amalgamation with mercury to form a dental material. More specifically, a multi-component composition having up to three distinct components.

Particles of the first component are substantially spherical in shape At least 30% by weight, of the multi-component composition is of these particles. They provide strength and corrosion resistance, and facilitate carving. On the other hand, no more than 90%, by weight, of the composition is of these particles. They tend to make it more difficult to condense the composition. In most instances, these particles are present in an amount of from 40 to 75%. The word spherical, as used herein, is meant to include particles which are spherical in shape as well as those which are spherical in shape with other spherical particles adhered to them.

Particles of the second component are mechanically worked to increase the surface area to volume ratio of the particles. The surface area to volume ratio of the particles of the second component is greater than the surface area to volume ratio of the particles of the first component. At least 10%, by weight, of the multi-component composition is of these particles. They provide for better adaption of an amalgam to a cavity and facilitate condensing of the composition. On the other hand, no more than 70%, by weight, of the composition is of these particles. Strength and corrosion resistance decrease and carved surfaces are rougher (thereby increasing the tendency for plaque formation) with increasing percentages. In most instances, these particles are present in an amount of from 25 to 55%.

The particles of both the first and second components are alloys of silver, tin and copper. They typically contain, by weight, at least 30% silver, at least 20% tin and at least 10% copper. More specifically, they contain from 30 to 70% silver, 20 to 35% tin, 10 to 40% copper, up to 2% noble metal (palladium, platinum, gold, ruthenium, rhodium, osmium, iridium), up to 4% zinc, up to 6% indium, up to 5% manganese, up to 2% aluminum, up to 5% gallium, and up to 3% mercury. The specific chemistry of the first component may be the same as or dissimilar to that of the second component. Each of the first and second components should be, in and by itself, free or substantially free of a tendency to form gamma two phase. Copper is preferably maintained at levels below 25% as copper has a tendency to darken restorations.

Particles of the third component are present in an amount of up to 15%, by weight, and generally in an amount of from 2 to 12%. The particles are either pure silver and/or an alloy containing at least 80% silver, by weight; e.g., an alloy of silver and tin or an alloy of silver and zinc. Sufficient silver must be present to form enough gamma one phase to substantially overcome the shrinkage caused by the first and second components. This will, in turn, lessen leakage. Post operative sensitivity and possible reoccurrence of decay are attributable to leakage.

The amalgam of the present invention is generally characterized by a one hour compressive strength of at least 29,000, and preferably 31,000 pounds per square inch. It is formed by triturating from 30 to 56% of mercury with from 44 to 70% of the multi-component composition of the present invention. Triturating is performed in accordance with procedures well known to those skilled in the art. Mercury is usually present in amounts of from 37 to 50%.

The multi-component composition of the present invention is produced in accordance with the following steps: producing a melt of a first component containing, by weight, at least 30% silver, at least 20% tin and at least 10% copper; atomizing the melt of the first component, thereby forming particles of the first component; collecting the particles of the first component; heat treating the particles of the first component to obtain desired working time; producing a melt of a second component containing, by weight, at least 30% silver, at least 20% tin and at least 10% copper; atomizing the melt of the second component thereby forming particles of the second component; collecting the particles of the second component; mechanically working the particles of the second component so as to increase the surface area to volume ratio of the particles; heat treating the particles of the second component to obtain desired working time; providing particles of a third component of silver or an alloy containing at least 80%, by weight, of silver; heat treating, if necessary or desirable, the particles of the third component to obtain desired working time; and blending the particles of the first component with the particles of the second component and the particles of the third component so as to produce a multi-component composition containing from 30 to 90%, by weight, of the first component, from 10 to 70%, by weight, of the second component and up to 15%, by weight, of the third component. The first and second component can be atomized in any manner known to those skilled in the art, providing that in the case of the first component, spherical particles are produced. These means include gas atomization, water atomization and spinning disc atomization. Gas atomization of the first component is preferred. Typical gas atomizing mediums are argon and nitrogen. The gas atomized powder can be dry or wet collected. The third component is preferably, but not necessarily, atomized. Various means for mechanically working the second component are also known to those skilled in the art. These means include hammer mills, rod mills and ball mills. Ball milling for at least thirty minutes is generally called for. Times in excess of one hour are preferred. Working times cannot, however, be precisely set forth as they are dependent upon various factors including the nature of the material being worked and the type of apparatus being used. A protective atmosphere may be employed during mechanical working.

Should a two component composition be desired, in contrast to that discussed in the preceding section, the steps pertaining to the third component are eliminated. A multi-component composition with all three components is, nevertheless, the preferred embodiment of the present invention.

The following examples are illustrative of several aspects of the invention.

EXAMPLE I

Three two-component compositions (Compositions A, B and C) were prepared. The overall chemistry of the compositions was very similar. Each of the compositions contained approximately 50% silver, 20% copper and 30% tin, with a palladium addition of less than 0.55%. The make-up of the compositions appears hereinbelow in Table I.

TABLE I

| COMPOSITION | |
|---|---|
| A. | 60% gas atomized spherical particles |
| | 40% lathe cut particles |
| B. | 60% gas atomized spherical particles |
| | 40% ball milled, gas atomized particles |
| C. | 60% gas atomized spherical particles |
| | 40% ball milled, water atomized particles |

Composition B was ball milled for one hour. Composition C was ball milled for two hours. All of the gas atomized particles were wet collected.

Each composition was heat treated to produce a "short" and a "long" carve time, and amalgamated with from 43 to 48% mercury. Carve time is the period from amalgamation to the time when the material will chip rather than cut or carve smoothly. The compositions with the "short" carve time are identified as $A_1$, $B_1$ and $C_1$. The compositions with the "long" curve time are identified as $A_2$, $B_2$ and $C_2$. The carve times appear hereinbelow in Table II.

TABLE II

| COMPOSITION | CARVE TIME (minutes) |
|---|---|
| $A_1$ | 5.75 |
| $B_1$ | 6.25 |
| $C_1$ | 6.0 |
| $A_2$ | 7.5 |
| $B_2$ | 8.25 |

TABLE II-continued

| COMPOSITION | CARVE TIME (minutes) |
| --- | --- |
| $C_2$ | 8.25 |

Compositions $A_1$, $B_1$ and $C_1$ were tested for compressive strength (1 hour and 24 hour), creep (24 hour) and condensation resistance. The results of the tests appear hereinbelow in Table III.

TABLE III

| COMPOSITION | COMPRESSIVE STRENGTH (pounds per square inch) | | CREEP (%) | CONDENSATION RESISTANCE (millimeters) |
| --- | --- | --- | --- | --- |
| | 1 HOUR | 24 HOURS | | |
| $A_1$ | 27,000 | 61,000 | 0.08 | 0.5 |
| $B_1$ | 46,000 | 78,000 | 0.03 | 0.7 |
| $C_1$ | 33,000 | 71,000 | 0.05 | 0.6 |

Compositions $B_1$ and $C_1$ displayed superior compressive strength to Compositions $A_1$, and creep and condensation resistance comparable thereto. This is most significant insofar as Compositions $B_1$ and $C_1$ do not contain lathe-cut particles with their inherent disadvantages as discussed hereinabove.

Compositions $A_2$, $B_2$ and $C_1$ were tested for compressive strength (1 hour and 24 hour), creep (24 hour) and condensation resistance. The results of the tests appear hereinbelow in Table IV.

TABLE IV

| COMPOSITION | COMPRESSIVE STRENGTH (pounds per square inch) | | CREEP (%) | CONDENSATION RESISTANCE (millimeters) |
| --- | --- | --- | --- | --- |
| | 1 HOUR | 24 HOURS | | |
| $A_2$ | 26,000 | 64,000 | N.A.* | 0.7 |
| $B_2$ | 41,000 | 75,000 | 0.04 | 0.7 |
| $C_2$ | 34,000 | 75,000 | 0.06 | 0.6 |

*not available

Compositions $B_2$ and $C_2$ displayed superior compressive strength to Compositions $A_2$, and condensation resistance comparable thereto. This is, again, most significant insofar as Compositions $B_2$ and $C_2$ do not contain lathe-cut particles with their inherent disadvantages as discussed hereinabove.

Condensation resistance measurements were made in accordance with the test (modified by subtracting the original height) described in an article entitled, "Measurement of Resistance of Amalgam Mixes to Condensation." The article authored by H. Ogura, F. Hadavi and K. Asgar appeared in the August, 1983 issue of the Journal of Dental Research.

EXAMPLE II.

Compositions $D_1$, $E_1$ and $E_2$ were amalgamated with from 43 to 48% mercury and tested for condensation resistance. The overall chemistries of these compositions were very similar to those of Compositions A, B and C. Compositions $D_1$, $E_1$ and $E_2$ were 100% gas atomized. None of these compositions were ball milled. Composition $D_1$ was wet collected. Compositions $E_1$ and $E_2$ were dry collected. The carve times for Compositions $D_1$, $E_1$ and $E_2$ were respectively 6, 6 and 7.5 minutes. The condensation resistance for each appears hereinbelow in Table V.

TABLE V

| COMPOSITION | CONDENSATION RESISTANCE (millimeters) |
| --- | --- |
| $D_1$ | 1.4 |
| $E_1$ | 1.0 |
| $E_2$ | 1.4 |

Note that the condensation resistance for Compositions $D_1$, $E_1$ and $E_2$ is significantly less (lower numbers indicate greater resistance) than that for Compositions $B_1$, $B_2$, $C_1$ and $C_2$. This is very significant, especially with respect to Compositions $B_1$ and $D_1$, since the only significant difference between Compositions $B_1$ and $D_1$ is the fact that a portion of Composition $B_1$ was ball milled.

EXAMPLE III.

Compositions $B_1$, $B_2$, $C_1$ and $C_2$ were modified to include 8% of a high silver alloy (95% silver, 5% tin). The newly created compositions were identified as $F_1$, $F_2$, $G_1$ and $G_2$. Compositions $F_1$, $F_2$, $G_1$ and $G_2$ respectively corresponded to modified versions of Compositions $B_1$, $B_2$, $C_1$ and $C_2$.

The carve times for Compositions $F_1$, $F_2$, $G_1$ and $G_2$ after amalgamation with from 43 to 48% mercury, appear hereinbelow in Table VI.

TABLE VI

| COMPOSITION | CARVE TIME (minutes) |
| --- | --- |
| $F_1$ | 5.75 |
| $G_1$ | 5.5 |
| $F_2$ | 7.75 |
| $G_2$ | 6.5 |

Compositions $B_1$, $B_2$, $C_1$, $C_2$, $F_1$, $F_2$, $G_1$ and $G_2$ were tested for dimensional change (24 hour) and leakage at 20 psig. The results of the tests appear hereinbelow in Table VII.

TABLE VII

| COMPOSITION | DIMENSIONAL CHANGE (microns per centimeter) | LEAKAGE (milliliters er minute) |
| --- | --- | --- |
| $B_1$ | −1.1 | 2.0 |
| $B_2$ | −3.4 | 3.1 |
| $C_1$ | −2.5 | 1.9 |
| $C_2$ | −2.9 | 2.6 |
| $F_1$ | 2.45 | 1.2 |
| $F_2$ | 1.7 | 0.9 |
| $G_1$ | 1.5 | 0.6 |
| $G_2$ | 1.2 | 0.4 |

Compositions $F_1$, $F_2$, $G_1$ and $G_2$, with the high silver alloy addition, expanded whereas Compositions $B_1$, $B_2$, $C_1$ and $C_2$, which did not have the high silver addition, contracted. Leakage, most notably, was significantly lower for Compositions $F_1$, $F_2$, $G_1$ and $G_2$ than for Compositions $B_1$, $B_2$, $C_1$ and $C_2$. Post operative sensitivity and possible reoccurrence of decay are attributable to leakage.

Leakage measurements were made in accordance with the test described in an article entitled, "Marginal Leakage of Dental Amalgam." The article authored by F. Fanian, F. Hadavi and K. Asgar appeared in the Aug. 11, 1983 issue of Operative Dentistry.

Compositions $F_1$ and $F_2$ were tested for compressive strength (1 hour and 24 hour), creep (24 hour) and condensation resistance. The results of the tests appear hereinbelow in Table VIII.

TABLE VIII

| COMPO-SITION | COMPRESSIVE STRENGTH (pounds per square inch) | | CREEP (%) | CONDENSATION RESISTANCE (millimeters) |
| --- | --- | --- | --- | --- |
| | 1 HOUR | 24 HOURS | | |
| $F_1$ | 42,000 | 70,000 | 0.05 | 0.6 |
| $F_2$ | 33,000 | 73,000 | 0.04 | 0.7 |

Compositions $F_1$ and $F_2$ displayed superior compressive strength to Compositions $A_1$ and $A_2$ (Example I), and creep and condensation resistance comparable thereto. This is most significant insofar as Compositions $F_1$ and $F_2$ do not contain lathe-cut particles with their inherent disadvantages as discussed hereinabove.

It will be apparent to those skilled in the art that the novel principles of the invention disclosed herein in connection with specific examples thereof will suggest various other modifications and applications of the same. It is accordingly desired that in construing the breadth of the appended claims they shall not be limited to the specific examples of the invention described herein.

We claim:

1. A method for producing a multi-component composition suitable for amalgamation with mercury to form a dental material, which method comprises the steps of: producing a melt of a first component containing, by weight, at least 30% silver, at least 20% tin and at least 10% copper; atomizing said melt of said first component, thereby forming particles of said first component; collecting said particles of said first component; heat treating the particles of said first component thereby obtaining a desired carve time; producing a melt of a second component containing, by weight, at least 30% silver, at least 20% tin and at least 10% copper; atomizing said melt of said second component thereby forming particles of said second component; collecting said particles of said second component; mechanically working said particles of said second component so as to increase the surface area to volume ratio of the particles of the second component, the surface area to volume ratio of the worked particles of the second component being greater than the surface area to volume ratio of the particles of the first component; heat treating the particles of said second component thereby obtaining a desired carve time; and blending said particles of said first component with said particles of said second component so as to produce a multi-component composition containing from 30 to 90%, by weight, of said first component and from 10 to 70%, by weight, of said second component.

2. A method for producing a multi-component composition according to claim 1 wherein said particles of said second component are mechanically worked for at least thirty minutes.

3. A method for producing a multi-component composition according to claim 2, wherein said particles of said second component are mechanically worked for at least one hour.

4. A method for producing a multi-component composition according to claim 1, wherein said mechanical working is ball milling.

5. A method for producing a multi-component composition according to claim 4, wherein said second component is ball milled for at least thirty minutes.

6. A method for producing a multi-component composition according to claim 1, including the steps of: providing particles of a third component consisting essentially of a member selected from the group consisting of silver and alloy powder containing at least 80%, by weight, silver; and blending said particles of said first component with said particles of said second component and said particles of said third component so as to produce a multi-component composition containing from 30 to 90%, by weight, of said first component, from 10 to 70%, by weight, of said second component and up to 15%, by weight, of said third component.

* * * * *